United States Patent [19]
Hirai et al.

[11] Patent Number: 5,795,791
[45] Date of Patent: Aug. 18, 1998

[54] METHOD OF DETERMINING CALIBRATION CURVE AND ANALYSIS METHOD AND APPARATUS USING THE SAME

[75] Inventors: Kikuo Hirai; Yoshihiko Makino, both of Saitama, Japan

[73] Assignee: Fuju Photo Film Co., Ltd., Kanagawa, Japan

[21] Appl. No.: 780,286

[22] Filed: Jan. 8, 1997

[30] Foreign Application Priority Data

Jan. 9, 1996 [JP] Japan ..................................... 8-018299

[51] Int. Cl.$^6$ ........................ G01N 33/53; G01N 33/566
[52] U.S. Cl. ........................ 436/501; 435/7.92; 435/967; 436/536; 436/542
[58] Field of Search ........................ 435/4, 7.92, 7.93, 435/7.94, 7.95, 967, 542; 436/501, 504, 536, 543, 547

[56] References Cited

PUBLICATIONS

Rodbard, et al—Statistical Analysis of Radioimmunoassays and Immunoradiometric (Labelled Antibody) Assays—A generalized weighted, iterative least-squares method for logistic curve fitting—pp. 165–192—IAEA-SM-177/208.

Rodbard, et al—"Rapid calculation of radioimmunoassay results"—J. Lab.& Clin. Med., vol. 74 No. 5, pp. 770–781, Nov. 1969.

Canellas et al., *J. Immunol. Methods* 47:375–385, 1981.

Kronvall et al., *APMIS* 99:295–306, 1991.

*Primary Examiner*—Robert D. Budens
*Attorney, Agent, or Firm*—McAulay Fisher Nissen Goldberg & Kiel, LLP

[57] ABSTRACT

One sigmoid calibration curve is split into three parts of low concentration region represented by a high degree function, intermediate concentration region represented by an exponential function and high concentration region represented by a high degree function according to the present invention. The boundary condition of the adjacent two functions is set so that the two functions have an equal slope at the boundary point; thereby, regression functions of the calibration curves in respective regions are found. The number of standard samples for finding a calibration curve can be reduced while the calibration curve found is of high accuracy.

9 Claims, 8 Drawing Sheets

METHOD OF DETERMINING CALIBRATION CURVE AND ANALYSIS METHOD AND APPARATUS USING THE SAME

BACKGROUND OF THE INVENTION

1. Field of the Invention

The present invention relates to a method of determining a calibration curve and an analysis method and apparatus using this calibration curve. Particularly, the present invention relates to a method of determining a regression function of a calibration curve for quantitative analysis of an analyte, with good accuracy in all the concentration region, when the calibration curve having a sigmoidal shape is used.

2. Description of the Related Art

In the conventional quantitative analysis of an analyte contained in a liquid sample, the concentration of the analyte in a test sample is determined from an analytical measured value (absorbency, transmitting or reflected optical density, other physical measuring quantity, or a signal indicating such a physical measuring quantity), after it is subjected to a proper chemical or enzymatic reaction. In such a method, it is common practice to determine the concentration of an analyte by using a calibration curve (also commonly referred to as standard curve or working curve) which has been preliminarily drawn by plotting the interrelation between the known concentrations of the analyte in the standard samples and the analytical measured values such as optical densities of the standard samples. When the calibration curve has an adequate linearity over a wider range in the region of quantitative analysis, the calibration curve can be prepared with a relatively smaller number of standard samples, which are near the upper limit, lower limit and in the intermediate point in the determination range of the quantitative analysis.

In practice, however, there are many calibration curves which are not linear in general. Examples of such calibration curves include those in immunological reactions such as enzyme immunoassay (EIA). In the immunoassay, the antigen-antibody reaction, which is the basis of the measurement, is essentially reversible in accordance with the law of mass action; hence, the calibration curve tends to be S-shaped sigmoid. This sigmoid type of calibration curve is also found in an enzyme reaction system in which the binding constant between the enzyme and the substrate varies due to formation of the enzyme-substrate complex, and in an allosteric enzyme reaction system involving regulatory function such as end-product inhibition. Furthermore, in the enzyme immunoassay, the shape of calibration curve varies easily depending on the type of the measurement system and the reaction condition. In addition, because the enzyme immunoassay is the ultramicro analysis method for micro substance, measured data have relatively broad dispersion. In the enzyme immunoassay, therefore, a large number of standard samples covering the entire determination range in the quantitative analysis have to be prepared and analyzed to draw a calibration curve.

In the field of clinical examinations necessitating quickness, economy and simplicity, it has been desired to prepare a calibration curve of high accuracy with a possible minimum number of standard samples. Hence, tries to prepare a calibration curve have been made up to now by getting a regression formula, from which the calibration curve is prepared with measurement values of a smaller number of standard samples.

A regression model of a calibration curve may be basically classified into two types: theoretical formula and empirical formula. Since a theoretical formula is rarely applicable to practical cases and has difficulty in statistical handling usually due to a complicated non-linear function of higher degree, an empirical formula based on an actual measurement is often used. Empirical formulae may also be classified basically into two types. One is based on a non-split-plot experiment, in which a single regression function covers a whole calibration curve. The other is based on a split-plot experiment, in which the calibration curve is segmented and a number of regression equations are calculated for each segmented portion.

Split-plot experiments include: a linear interpolation method in which interpolation is made on the basis of linear segments obtained by connecting two adjacent points on a calibration curve by a straight line; and a fitting method by spline function in which all intervals between two adjacent points are covered by cubic polynominal functions, maintaining continuity with adjoining functions. Both methods as well as the other approaches cannot fit S-shaped curve of calibration satisfactorily without many analytical measured values.

As non-split-plot experiments, there are known a regression method using a logistic curve; a regression method using logit-log conversion formula; a method using an equilateral hyperbola; and a method applying a polynomial expression of cubic or higher degree to a sigmoid calibration curve. Among them, the method using an equilateral hyperbola cannot be fitted well to an S-shaped calibration curve.

Logistic curves have been known as an empirical formula for S-shaped curves. A most prevalent logistic curve is represented by following formula having four coefficients:

$$y = \frac{a-d}{1+(x/c)^b} + d$$

wherein, x: concentration, y: analytical measured value (data such as optical density), and a, b, c, and d : coefficients.

(Rodbard et al.: Statistical analysis of radioimmunoassays and immunoradiometric (labeled antibody) assays. A generalized, weighted, iterative, least-squares method for logistic curve fitting. Symposium on RIA and Related Procedures in Medicine, p165, Int. Atomic Energy Agency, Vienna, 1974)

This logistic curve is a sigmoid curve as shown in FIG. 1 and is excellent as a calibration curve model obtained from a small number of measurement points and standard samples, since this curve gives not only a linear part in its middle but also curve parts at both ends and furthermore an asymptotic part outside the end. Statistical treatment of this logistic curve is complicated, however, because the above formula which represents this curve is nonlinear and the regression of this formula requires an iterative least square method for. In addition, it is necessary to obtain the analytical measured value (signal, or ΔOD in the Example hereinafter) precisely when the amount of the antigen (concentration: x) is zero and infinity (∞) respectively. In order to obtain the measurement point for infinite amount of the antigen, it is required to prepare and store a standard sample containing a large excessive amount of the antigen. As a matter of fact, this is extremely difficult as compared to preparation and storage of standard samples containing a normal amount of the antigen (analyte). Furthermore, it is likely that the signal changes due to hook effect (also referred to as prozone effect) and the calibration curve has a maximum value (or minimum value) when an excessive amount of the antigen exists against antibody at an immunoassay. In such a case, the signal for infinite amount of the antigen cannot be obtained.

A logit-log conversion is to apply a logit conversion for the vertical axis (indicated or measured value) of a calibration graph and apply a logarithm conversion to the horizontal axis (concentration: dose) of the calibration graph. Thus, a S-shaped curve can be linearized by use of the following simple linear polynominal:

$$Y = a + bX$$

$$\left[ Y = \text{logit } y = \log \frac{y}{1-y} \; ; \quad y = \frac{B_X - N}{B_0 - N} \right]$$
$$\left[ X = \log x; \quad x = \text{"dose"} \right]$$

wherein, $B_0$ and $B_x$ are the measured values at concentration 0 (zero) and concentration x respectively; and N is the measured value at infinite concentration.

(Rodbard et al.: Rapid calculation of radioimmunoassay results, J. Lab. Clin. Med., 74, p770, 1969)

The logit-log conversion can be performed in the simpler regression by a simple least square method and is superior to logistic curve described above. Even this logit-log conversion, however, has a defect in that more deviation from the linear line will occur, unless both signal $B_0$ at zero concentration and signal N at infinite concentration are determined accurately. In other words, it is difficult to prepare a calibration curve when the number of measurement points is small.

A most prevalent conventional method is approximation of a sigmoid calibration curve by a cubic (three-degree) polynomial. This method is effective in case of using only a linear part of an S-shaped curve as the working range of a calibration curve. However, this method cannot fit the whole range of data points including not only the linear part in the S-shaped curve but also curve parts at both ends and furthermore an asymptotic part outside the end. Thus, an effort to improve accuracy in the middle of the sigmoid curve results in lowering accuracy at both ends. On the contrary, an effort to apply both ends of the curve as working ranges results in sacrificing accuracy to a certain extent at the middle part of the curve. These are not improved even when more measurement points of standard samples are used. There has been a certain limit to a method of applying one model (function) to a whole calibration curve.

OBJECTS AND SUMMARY OF THE INVENTION

The present invention has been accomplished in view of the aforementioned circumstances, and a first object thereof is to provide an improved method for a quantitative analysis of an analyte with high accuracy at any of low, intermediate and high concentration regions.

A second object of the present invention is to provide a method of determining a regression function of a calibration curve for a wide range covering low, intermediate and high concentration regions by use of a small number of standard samples, with simple and quick process.

A third object of the present invention is to provide an apparatus for a quantitative analysis of an analyte in a sample, by which the calibration curve mentioned above can be prepared simply and quickly and the quantitative analysis can be performed with high accuracy at a wide range covering all the concentration region.

The first object of the present invention is attained by a method for quantitative analysis of an analyte in a sample by referring a calibration curve prepared by using the interrelation between the known concentrations of the analyte in standard samples and analytical measured values of the standard samples:

wherein said calibration curve is split into at least three parts as followings:
  (a) a part of the calibration curve for a low concentration region which is represented by a multi-degree function,
  (b) a part of the calibration curve for an intermediate concentration region which is represented by an exponential function, and
  (c) a part of the calibration curve for a high concentration region which is represented by a multi-degree function;

and wherein the adjacent two parts of the calibration curve have an identical slope in the boundaries of respective concentration regions of the above.

The second object of the present invention is attained by a method of determining a regression function of a calibration curve for quantitative analysis of an analyte, the calibration curve being prepared by using the interrelation between the known concentrations of the analyte in standard samples and analytical measured values of the standard samples, said method comprising steps of:

(a) representing the calibration curve for a low concentration region by a multi-degree function;
  (b) representing the calibration curve for an intermediate concentration region by an exponential function;
  (c) representing the calibration curve for a high concentration region by a multi-degree function; and
  (d) assuming boundary conditions of respective concentration regions of the above that the adjacent two parts of the calibration curve have an identical slope at the boundary points, whereby the functions of the calibration curve for respective concentration regions are determined.

Conveniently, quadratic (2nd degree) functions are selected as the multi-degree functions which represent the low and high concentration regions of the calibration curve, since the number of data points (standard samples) for regressing the functions of these parts can be made smaller. Even with such a smaller number of data points, the accuracy can be maintained without substantial sacrifice since continuity is secured by the boundary conditions with the adjacent intermediate concentration region. However, the multi-degree functions may be of cubic or higher degree depending on the curvature at the low or high concentration region of the calibration curve.

In the case that a quadratic function is used for representing the partial calibration curve for the high and low concentration regions, the regression function of the entire calibration curve is able to be prepared by the following steps of (a) through (g). That is, (a) plotting respective concentrations ($p_i$) of the analyte in the standard sample and the logarithmic values ($\log q_i$) of the corresponding analytical measured values ($q_i$) on the rectangular coordinate system;
  (b) finding an intermediate concentration region ($p_1 - p_2$) which constitutes a linear portion in this semi-logarithmic graph;
  (c) expressing the part of calibration curve of this intermediate concentration region ($p_1 - p_2$) as $Y = \exp(b \cdot X + d)$ which means $$X = (\ln Y - d)/b \tag{1}$$

wherein
Y is the analytical measured value ($q_i$) such as optical density or other physical quantity.
X is the concentration of the analyte in the standard sample ($p_i$), and
b and d are coefficients;

(d) expressing the part of calibration curve of the low concentration region (from the minimum concentration $p_0$ in the standard samples to the concentration $p_i$) as $$X = e \cdot Y^2 + f \cdot Y + g \tag{2}$$

wherein e, f and g are coefficients;

(e) expressing the part of calibration curve of the high concentration region (from the concentration $p_2$ to the maximum concentration $p_3$ in the standard samples) as $$X = l \cdot Y^2 + m \cdot Y + n \tag{3}$$

wherein l, m and n are coefficients;

(f) setting boundary conditions where the differentiated value (dX/dY) of Equation (1) at the coordinate ($p_1$, $q_1$) is equal to the differentiated value (dX/dY) of Equation (2) at the coordinate ($p_1$, $q_1$) and where the differentiated value (dX/dY) of Equation (2) at the coordinate ($p_2$, $q_2$) is equal to the differentiated value (dX/dY) of Equation (3) at the coordinate ($p_2$, $q_2$); and (g) calculating respective coefficients in Equations (1), (2) and (3) and finding therefrom the continuous regression function of the calibration curve for the whole concentration region covering from $p_0$ to $p_3$.

The steps (a) and (b) for finding the intermediate concentration region ($p_1$–$p_2$) is not necessarily done together with the steps (c) to (g) to be followed. That is, the intermediate concentration region ($p_1$–$p_2$) may be set as a range between the concentrations of both ends (or concentrations near both ends) of an intermediate concentration region which can be represented by an exponential function for measuring the analyte. In this case, the intermediate concentration region is to be found preliminarily for individual lot of assay kit or individual analyzing apparatus. And the standard samples having concentrations $p_1$ and $p_2$, which are ends of the intermediate concentration region, is supplied or distributed to the users with the individual assay kit or individual analyzing apparatus.

This case of the present invention may be defined as a method of preparing a regression function of calibration curve comprising the following steps of:

(a) providing an intermediate concentration region ($p_1$–$p_2$) which is preliminarily defined as the region of linear portion in a semi-logarithmic graph in which respective concentrations ($p_i$) of the analyte in the standard samples and the logarithmic values (log $q_i$) of the corresponding analytical measured values ($q_i$) on a rectangular coordinate system, said linear portion having the most proximate concentrations $p_1$ and $p_2$ at both ends;

(b) expressing the part of calibration curve of an intermediate concentration region ($p_1$–$p_2$) as $Y = \exp(b \cdot X + d)$ which means $$X = (\ln Y - d)/b \tag{1}$$

wherein Y is the analytical measured value ($q_i$) such as optical density or other physical measuring quantity.
X is the concentration of the analyte in the standard sample ($p_i$), and
b and d are coefficients;

(c) expressing the part of calibration curve of the low concentration region (from the minimum concentration $p_0$ in the standard sample to the concentration $p_1$) as $$X = e \cdot Y^2 + f \cdot Y + g \tag{2}$$

wherein e, f and g are coefficients;

(d) expressing the part of calibration curve of the high concentration region (from the concentration $p_2$ to the maximum concentration $p_3$ in the standard sample) as $$X = l \cdot Y^2 + m \cdot Y + n \tag{3}$$

wherein l, m and n are coefficients;

(e) setting boundary conditions where the differentiated value (dX/dY) of Equation (1) at the coordinate ($p_1$, $q_1$) is equal to the differentiated value (dX/dY) of Equation (2) at the coordinate ($p_1$, $q_1$) and where the differentiated value (dX/dY) of Equation (2) at the coordinate ($p_2$, $q_2$) is equal to the differentiated value (dX/dY) of Equation (3) at the coordinate ($p_2$, $q_2$); and (f) calculating respective coefficients in Equations (1), (2) and (3) and finding therefrom the continuous regression function of the calibration curve for the whole concentration region covering from $p_0$ to $p_3$.

The third object of the present invention is attained by an apparatus for quantitative analysis of an analyte in a sample by referring a calibration curve prepared by using the interrelation between the known concentrations of the analytes in standard samples and analytical measured values of the standard samples, said apparatus comprising:

1) input means for inputting the known concentrations ($p_i$) of the analytes contained in plural standard samples and their analytical measured values ($q_i$);

2) a processor for receiving the data input from said input means and processing the operations mentioned below to determine a regression function of the calibration curve on the basis of the input ($p_i$) and ($q_i$),
said operations including steps of;

(a) expressing the part of calibration curve of an intermediate concentration region ($p_1$–$p_2$), which is defined as the region of linear portion in a semi-logarithmic graph in which respective concentrations ($p_i$) of the standard sample and the logarithmic values (log $q_i$) of the corresponding analytical measured values ($q_i$) on a rectangular coordinate system, said linear portion having the most proximate concentrations $p_1$ and $p_2$ at both ends, as $Y = \exp(b \cdot X + d)$ which means $$X = (\ln Y - d)/b \tag{1}$$

wherein
Y is the analytical measured value ($q_i$) such as optical density or other physical measuring quantity.

X is the concentration of the analyte in the standard sample ($p_i$), and b and d are coefficients;

(b) expressing the part of calibration curve of the low concentration region (from the minimum concentration $p_0$ in the standard sample to concentration $p_1$) as $$X = e \cdot Y^2 + f \cdot Y + g \quad (2)$$

wherein e, f and g are coefficients;

(c) expressing the part of calibration curve of the high concentration region (from concentration $p_2$ to the maximum concentration $p_3$ in the standard sample) as $$X = l \cdot Y^2 + m \cdot Y + n \quad (3)$$

wherein l, m and n are coefficients;

(d) setting boundary conditions where the differentiated value (dX/dY) of Equation (1) at the coordinate ($p_1$, $q_1$) is equal to the differentiated value (dX/dY) of Equation (2) at the coordinate ($p_1$, $q_1$) and the differentiated value (dX/dY) of Equation (2) at the coordinate ($p_2$, $q_2$) is equal to the differentiated value (dX/dY) of Equation (3) at the coordinate ($p_2$, $q_2$); and (e) calculating respective coefficients in Equations (1), (2) and (3) and finding therefrom the continuous regression function of the calibration curve for the whole concentration region covering from $p_0$ to $p_3$; and 3) a calibration curve generator for generating the calibration curve to be used for quantitative analysis of the analyte contained in a test sample, the calibration curve being prepared from the regression function determined by said processor.

DETAILED DESCRIPTION OF THE INVENTION

Figure 1:
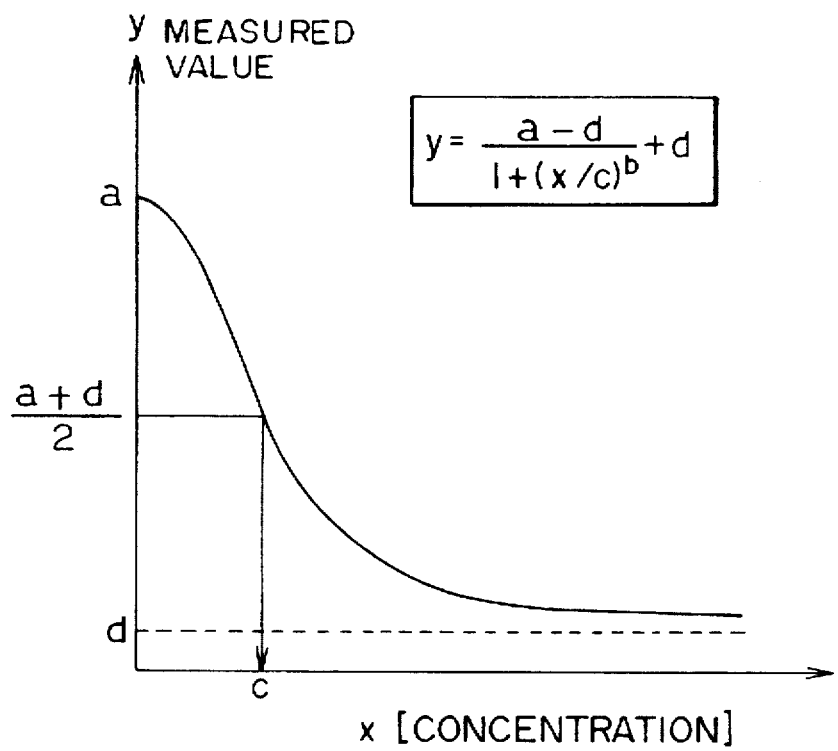
FIG. 1 is a schematic calibration curve in accordance with a conventional logistic curve model.

As discussed in the background section of the specification, it is difficult for a whole sigmoid calibration curve to be represented by only one function and at the same time to secure high accuracy over all the concentration regions. It might not be impossible if an extremely complicated function is introduced; however, such complexity needs a more number of coefficients for solution with resultant requirement for more number of standard samples for measurement.

According to the present invention, one sigmoid calibration curve is split into three parts of low, medium and high concentration regions and respective parts are represented by different functions. When functions are changed like this case, the accuracy varies abruptly near the boundary regions normally. For the purpose of avoiding such phenomenon, the boundary condition of the adjacent two functions is set such that the two functions have the same tangential line (slope) at the boundary point (point of contact) according to the present invention. Mathematically, the adjacent two functions have the same differentiated value at the boundary point. By this boundary condition, the adjacent two functions connect smoothly and the accuracy does not vary significantly between them. In addition, introduction of the boundary condition can save at least one measurement point (or standard sample) necessary for obtaining coefficients for the determination of the function of each concentration region.

The inventors have found that a sigmoid calibration curve has a middle concentration region which can be represented by an exponential function. On the basis of this finding, the middle concentration region is represented and regressed by an exponential function according to the present invention. In this intermediate concentration region, only two measurement points (standard samples) definitely determine the exponential function, as is seen from the fact that a straight line is obtained by plotting an exponential function on a semi-logarithmic graph. If the concentrations at both ends of the intermediate concentration region (or the concentrations close to them) are adopted as the concentration of the measurement points (standard samples), these data (concentrations or other analytical measured values) on the two measurement points can also be used as the data on the boundary points with adjacent low and high concentration regions. As the result, the number of measurement points (standard samples) necessary for determining the regression functions of whole calibration curve, can be made further smaller.

It is explained below that a sigmoid calibration curve has a middle concentration region which can be represented by an exponential function.

By using dry analytical elements for the analysis of CRP (C-reactive protein) used in the Working Example described herein after, scattering of color development (C.V.(%)) for these analytical elements was checked. Standard samples in liquid form of various CRP concentrations were spotted on to the analytical elements and were kept at 37° C. The optical density of the reflected light was measured at 650 nm from the PET support side of the element. Difference of the reflected optical density measured respectively after the lapse of 4 minutes and 6 minutes from spotting ($\Delta OD_{6-4}$:

also referred to as $dOD_{6-4}$, or dODr hereinafter and the attached drawings) was obtained. Fifty measurements of each concentration were carried out to obtain the average value ($dOD_{ave}$) standard deviation (S.D.) for each of the average values and coefficient of variation C.V.(=(S.D./$dOD_{ave}$)×100). TABLE 1 shows the results. The same CRP concentration listed in the TABLE 1 are for the experimental result of the other day.

TABLE 1

| CRP Concentration (mg/dL) | $dOD_{ave}$ | S.D. | C.V. (%) |
|---|---|---|---|
| 1.0 | 0.2536 | 0.0083 | 3.3 |
| 1.8 | 0.2027 | 0.0064 | 3.2 |
| 10.1 | 0.0828 | 0.0031 | 3.7 |
| 17.0 | 0.0730 | 0.0023 | 3.2 |
| 1.7 | 0.2326 | 0.0065 | 2.8 |
| 1.7 | 0.2336 | 0.0057 | 2.4 |
| 2.6 | 0.2096 | 0.0052 | 2.5 |
| 2.6 | 0.2136 | 0.0064 | 3.0 |
| 4.3 | 0.1767 | 0.0062 | 3.5 |
| 4.3 | 0.1728 | 0.0053 | 3.1 |
| Average | | | 3.1 |

Figure 2:
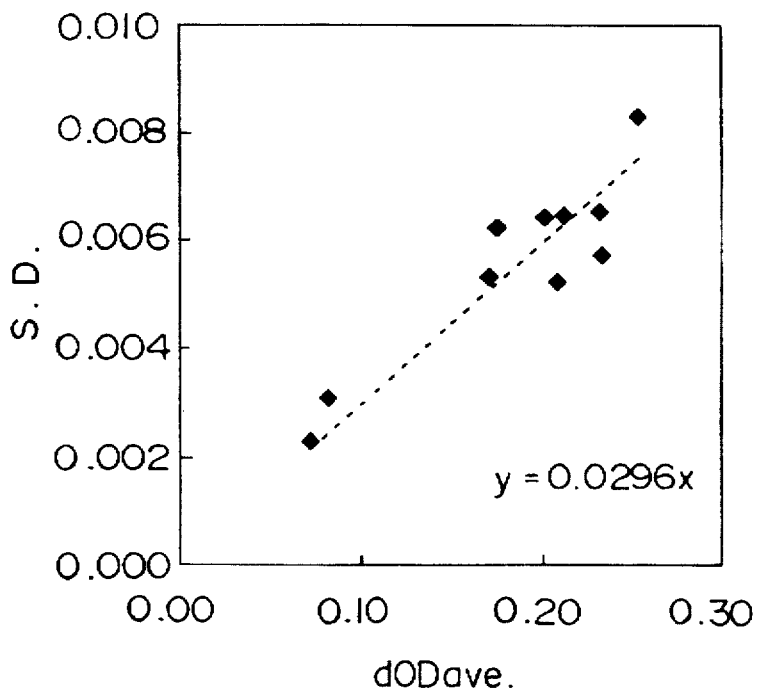
FIG. 2 is a correlation diagram between average analytical measured values ($dOD_{ave}$) in dry analytical elements for analyzing CRP at respective concentrations and their standard deviations (S.D.)

Regardless of the CRP concentration, the value of C.V. (%) was nearly constant (3% or so). A high correlation was noted, as shown in FIG. 2, between $dOD_{ave}$ and standard deviation (S.D.).

Figure 3:
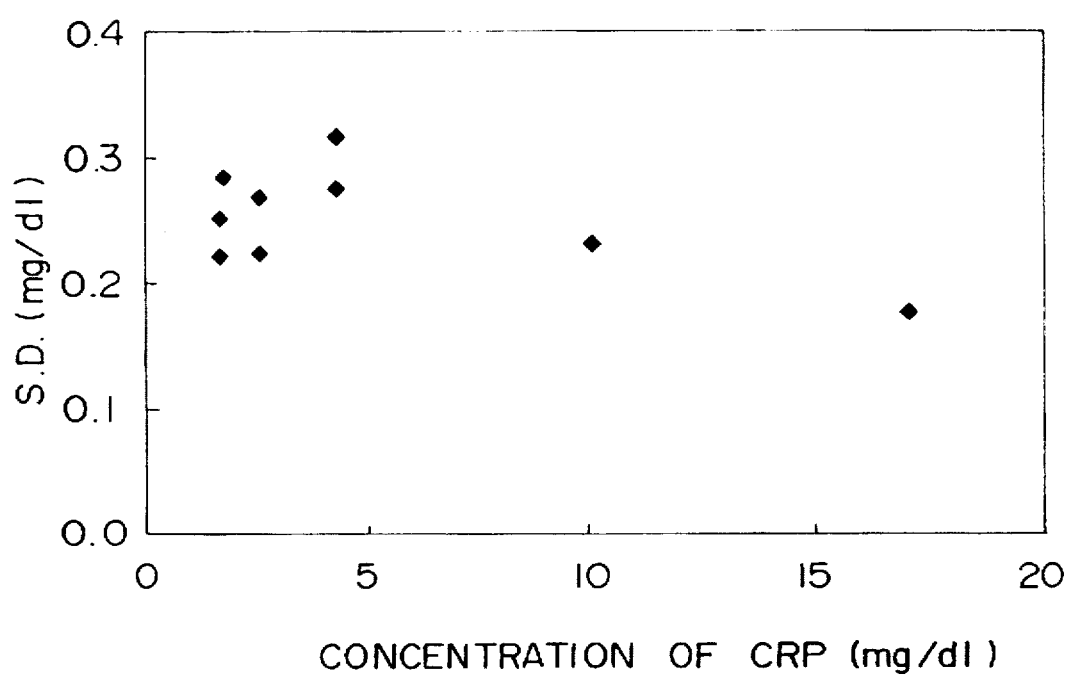
FIG. 3 is a diagram showing relationship between CPR concentrations, which are obtained by dry analytical elements for CRP analysis and read from the calibration curve, and standard deviations (S.D.) thereof.

A calibration curve was prepared from $dOD_{6-4}$ obtained in the above measurement. From this calibration curve, concentrations of CRP in respective samples were analyzed. The standard deviations (S.D.)s of the analytical values (concentrations) were shown in TABLE 2 and FIG. 3. In a concentration region up to 10 mg/dl at least, the standard deviation of the indicated values of CRP concentration was nearly constant (about 0.25).

TABLE 2

| CRP Concentration read from Calibration Curve (mg/dL) | S.D. (mg/dL) |
|---|---|
| 1.8 | 0.28 |
| 10.1 | 0.23 |
| 17.0 | 0.18 |
| 1.7 | 0.25 |
| 1.7 | 0.22 |
| 2.6 | 0.27 |
| 2.6 | 0.27 |
| 4.3 | 0.32 |
| 4.3 | 0.28 |
| Average | 0.25 |

Regardless of the CRP concentration, the variation C.V. of dODr and the standard deviation (S.D.) of the indicated values of CRP concentration read from the calibration curve were nearly constant. From these facts, a function of the calibration curve applicable under such conditions is devised.

A calibration curve function is $$y_0 = F(x_0)$$

for $dODr(y_0)$ at a given CRP concentration($x_0$) when the calibration curve F and the S.D. performance function G for the indicated value of concentration are set for the CRP concentration x and dODr y respectively. As discussed above, the C.V. of dODr is constant; hence, the standard deviation (S.D.) of dODr is $\alpha \cdot y_0$, when $dODr=y_0$, where $\alpha$ is a constant value (about 0.03 in this case as mentioned above).

Considering the differential function (F') of the calibration curve function (F), the relationship between S.D. of the CRP concentration (indicated) at a given CRP concentration ($x_0$) and S.D. of dODr (=$y_0$) is:

$$F'(x_0) = [S.D. \text{ of } dODr \text{ at } y_0]/[S.D. \text{ of indicated } CRP \text{ concentration at } x_0]$$
$$= \alpha \cdot y_0/G(x_0)$$

Substituting the S.D. performance function for G(x), F(x) can be solved as a differential equation. As a result of TABLE 2 and FIG. 3, G(x)=0.25 may be assumed. As a result of TABLE 1 and FIG. 2, $\alpha$=0.03 (3% when C.V. is shown as percentage). Hence.

$$F'(x_0)=0.03 \cdot F(x)/0.25$$

That is, $$F'(x_0)/F(x)=0.03/0.25=\text{constant}$$

Generalizing this by use of coefficients b and d, this can be represented in the form of:

$$F(x)=exp(b \cdot X+d)$$

Thus, it has been now found that the basic profile of calibration curve for analyzing CRP can be represented by an exponential function.

As seen, it can be understood that at least a part (intermediate concentration region as a matter of practice) of a sigmoid calibration curve can be represented by an exponential function. According to the present invention, a high concentration region and a low concentration region inserting the intermediate concentration region are represented by multi-degree functions, and their boundary conditions are so set that the two functions have the same slope (differentiated value at their boundary points); in this way, a regression function of a calibration curve can be prepared covering the whole concentration region. On the case where the low and high concentration regions are represented by guadratic (second degree) functions, the method of determining a regression function of a calibration curve according to the present invention is explained in details hereinafter.

Figure 4:
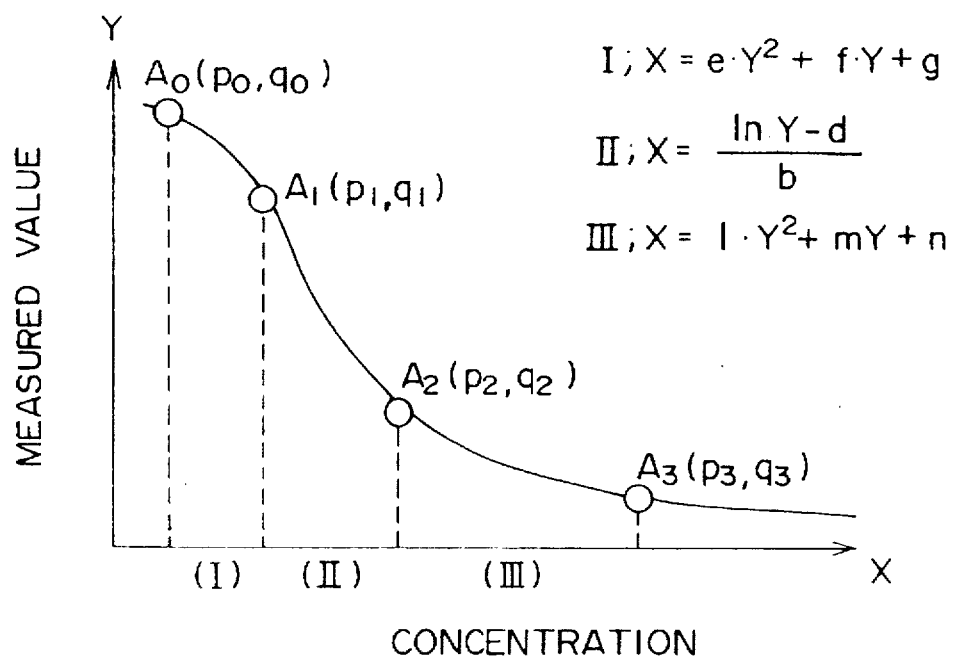
FIG. 4 is a schematic diagram explaining the principle of the method of determining a regression function of calibration curve according to the present invention.
Figure 5:
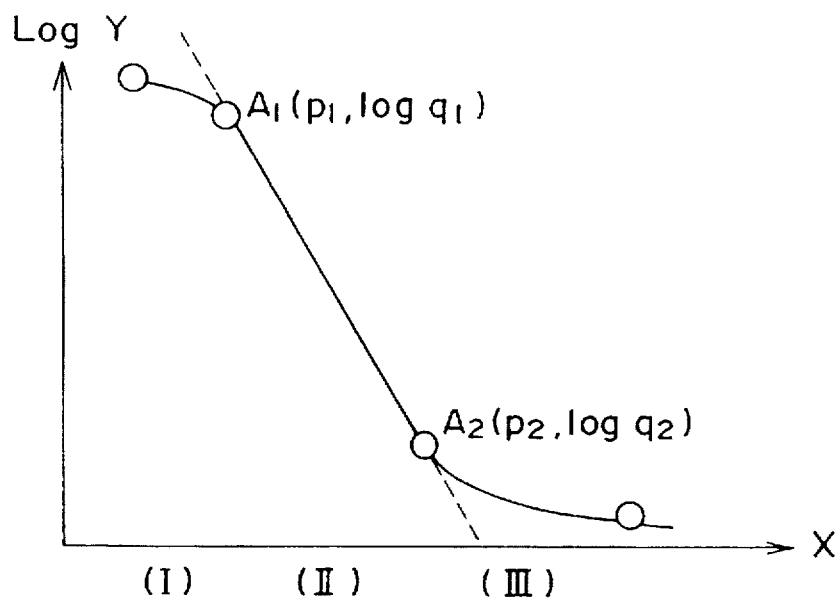
FIG. 5 is a schematic diagram, in which the vertical axis is of logarithm values, also explaining the principle of the present invention.

FIG. 4 is a schematic diagram of a typical sigmoid calibration curve. The axis of abscissa expresses concentration X and the axis of ordinate expresses analytical measured value Y (for example, dODr in Example). In FIG. 5, the vertical axis is of logarithm values of the measured value Y. For the sake of convenience in the explanation, four measurement data points $A_0$, $A_1$, $A_2$ and $A_3$ are plotted here. The concentrations of respective samples are $p_0$, $p_1$, $p_2$ and $p_3$ and their analytical measured values are $q_0$, $q_1$, $q_2$ and $q_3$. Zone II of $A_1-A_2$ at the intermediate concentration region $p_1-p_2$ constitutes a linear part on the semi-logarithmic graph shown in FIG. 5, and can be represented by an exponential function.

When Zone I ($p_0-p_1$: low concentration region) and Zone III ($p_2-p_3$: high concentration region) are represented by second degree functions, respective Zones are expressed as follows.

Zone II (Intermediate concentration region):

$$Y=exp(b \cdot X+d)$$

that is, $$X = (\ln Y - d)/b \tag{1}$$

wherein b and d are coefficients.

Zone II (Low concentration region):

$$X = e \cdot Y^2 + f \cdot Y + g \tag{2}$$

where e, f and g are coefficients.

Zone III (High concentration region):

$$X = l \cdot Y^2 + m \cdot Y + n \tag{3}$$

where l, m and n are coefficients.

In Zone II, the calibration curve passes through $A_1(p_1, q_1)$ and $A_2(p_2, q_2)$. Accordingly, $$\begin{aligned} b &= (\ln q_2 - \ln q_1)/(p_2 - p_1) \\ &= [\ln (q_2/q_1)]/(p_2 - p_1) \end{aligned} \tag{4}$$

$$\begin{aligned} d &= \ln q_2 - b \cdot p_2 \\ &= \ln q_2 - [(\ln q_2 - \ln q_1)/(p_2 - p_1)] \cdot p_2 \\ &= (p_2 \cdot \ln q_1 - p_1 \cdot \ln q_2)/(p_2 - p_1) \end{aligned} \tag{5}$$

Thus, coefficients b and d are easily found.

Respective coefficients in Zone I (low concentration region) are now to be found. The boundary condition for Zone I and Zone II is to have an equal slope or differentiated value (dX/dY) at the boundary point $A_1(p_1, q_1)$. Differentiating Equation (1) with respect to measured value Y, $$dX/dY = 1/(b \cdot Y) \tag{6}$$

Differentiating Equation (2), $$dX/dY = 2e \cdot Y + f \tag{7}$$

Since Equations (6) and (7) have an equal value at the boundary point $A_1(p_1, q_1)$, $$1/(b \cdot q_1) = 2e \cdot q_1 + f \tag{8}$$

On the other hand, the quadratic curve of Equation (2) passes through $A_0(p_0, q_0)$ and $A_1(p_1, q_1)$ in Zone I. Hence, $$p_0 = e \cdot q_0^2 + f \cdot q_0 + g \tag{9}$$

$$p_1 = e \cdot q_1^2 + f \cdot q_1 + g \tag{10}$$

The Equations (9) and (10) are combined to give the following equation, $$\begin{aligned} p_1 - p_0 &= e(q_1^2 - q_0^2) + f(q_1 - q_0) \\ &= (q_1 - q_0)[e(q_1 - q_0) + f] \end{aligned}$$

Dividing both members by $(q_1 - q_0)$, $$(p_1 - p_0)/(q_1 - q_0) = e \cdot (q_1 + q_0) + f \tag{11}$$

From Equations (8) and (11), $$\begin{aligned} 1/(b \cdot q_1) - (p_1 - p_0)/(q_1 - q_0) &= 2e \cdot q_1 - e(q_1 + q_0) \\ &= e(q_1 - q_0) \end{aligned}$$

Thus, $$e = [1/(b \cdot q_1) - (p_1 - p_0)/(q_1 - q_0)]/(q_1 - q_0) \tag{12}$$

From Equation (8), $$f = 1/(b \cdot q_1) - 2e \cdot q_1 \tag{13}$$

Accordingly coefficient f is determined from coefficient b (found from Equation (4)) and from coefficient e (found from Equation (12)).

The remaining coefficient g is found from Equation (9).

$$g = p_0 - e \cdot q_0^2 - f \cdot q_0 \tag{14}$$

As for Zone III (high concentration region: $A_2$–$A_3$), coefficients l, m and n are found similarly. Differential of Equation (3) at the boundary point $A_2(p_2, q_2)$ $$dX/dY = 2 \cdot l \cdot Y + m \tag{15}$$

is equal to dX/dY (=1/(b·Y)) of Equation (6). Hence, $$1/(b \cdot q_2) = 2 \cdot l \cdot q_2 + m \tag{16}$$

On the other hand, the quadratic curve of Equation (3) passes through points $A_2(p_2, q_2)$ and $A_3(p_3, q_3)$ in Zone III. Hence, $$p_2 = l \cdot q_2^2 + m \cdot q_2 + n \tag{17}$$

$$p_3 = l \cdot q_3^2 + m \cdot q_3 + n \tag{18}$$

Subtracting Equation (17) from Equation (18), $$\begin{aligned} p_3 - p_2 &= l(q_3^2 - q_2^2) + m(q_3 - q_2) \\ &= (q_3 - q_2)[l \cdot (q_3 + q_2) + m] \end{aligned}$$

Dividing both members by $(q_3 - q_2)$, $$(p_3 - p_2)/(q_3 - q_2) = l \cdot (q_3 + q_2) + m \tag{19}$$

Subtracting Equation (19) from Equation (16), $$\begin{aligned} 1/(b \cdot q_2) - (p_3 - p_2)/(q_3 - q_2) &= 2 \cdot l \cdot q_2 - l \cdot (q_3 + q_2) \\ &= l \cdot (q_2 - q_3) \end{aligned}$$

Thus, $$l = [1/(b \cdot q_2) - (p_3 - p_2)/(q_3 - q_2)]/(q_2 - q_3) \tag{20}$$

From Equation (16), $$m = 1/(b \cdot q_2) - 2 \cdot l \cdot q_2 \tag{21}$$

From Equation (17), $$n = p_2 - l \cdot q_2^2 - m \cdot q_2 \tag{22}$$

In summary, for Zone I (low concentration region: $p_0 \leq X \leq p_1$, $q_0 \geq Y \geq q_1$)

$$X = e \cdot Y^2 + f \cdot Y + g$$

for Zone II (intermediate concentration region: $p_1 \leq X \leq p_2$, $q_1 \geq Y \geq q_2$)

$$X = (\ln Y - d)/b$$

for Zone III (high concentration region: $p_2 \leq X \leq p_3$, $q_2 \geq Y \geq q_3$)

$$X = l \cdot Y^2 + m \cdot Y + n$$

and the coefficients are as follows.

$$b = (\ln q_2 - \ln q_1)/(p_2 - p_1) = \ln(q_2/q_1)/(p_2 - p_1)$$

$$d = \ln q_2 - b \cdot p_2 = (p_2 \cdot \ln q_1 - p_1 \cdot \ln q_2)/(p_2 - p_1)$$

$e=|1/(b\cdot q_1)-(p_1-p_0)/(q_1-q_0)|/(q_1-q_0)$ $f=1/(b\cdot q_1)-2e\cdot q_1$ $g=p_0-e\cdot q_0^2-f\cdot q_0$ $l=|1/(b\cdot q_2)-(p_3-p_2)/(q_3-q_2)|/(q_2-q_3)$ $m=1/(b\cdot q_2)-2\cdot l\cdot q_2$ $n=p_2-l\cdot q_2^2-m\cdot q^2$ As explained, a calibration curve depicting a sigmoid curve is, according to the present invention, split into 3 parts: a part for a low concentration region which is represented by a high degree function; a part for an intermediate concentration region which is represented by an exponential function; and a part for a high concentration region which is represented by a high degree function. The adjacent two parts are so made as to have an equal slope at the boundary point as the boundary condition. In this way, a regression function of the calibration curve for covering all of the respective concentration regions is determined. Only a small number of the standard samples for measurement in obtaining the calibration curve are required in this procedure. Furthermore, accuracy of the resultant calibration curve is high throughout the whole concentration regions.

The regression function of the calibration curve determined in this way can practically be used even for concentrations lower than the minimum concentration ($p_0$) used to determine the function for low concentration region and even for concentrations higher than the maximum concentration ($p_3$) used to determine the function for high concentration region.

Analysis Apparatus

Figure 6:
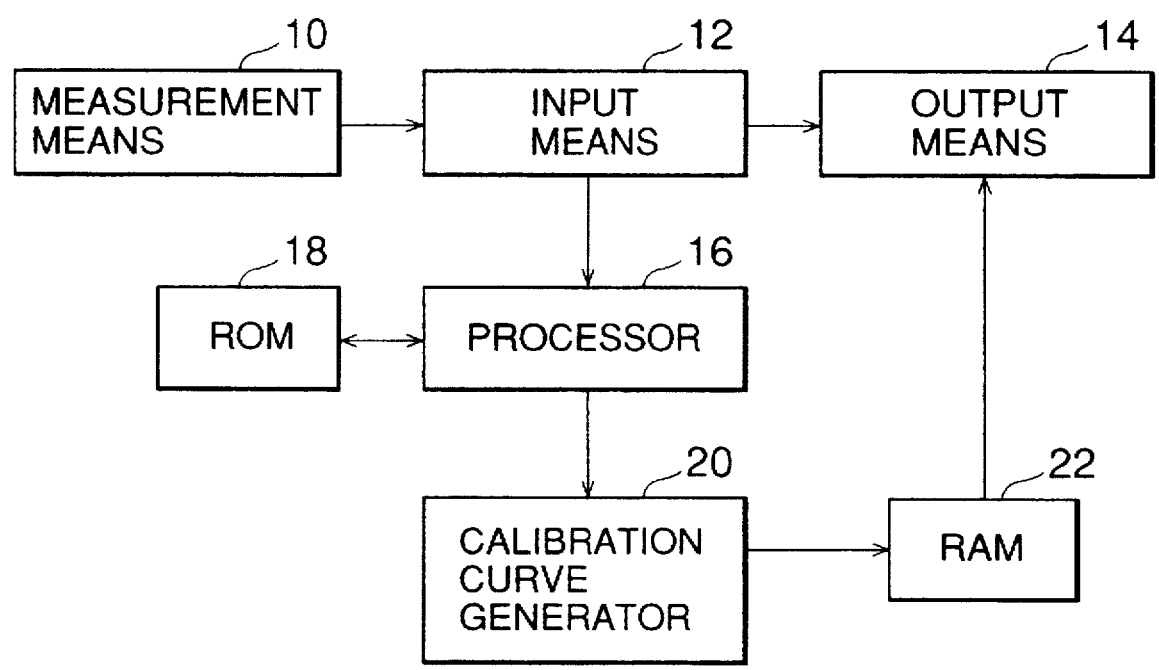
FIG. 6 is a block diagram showing a basic construction of an embodiment of the analyzing apparatus according to the present invention.

Now, an analyzing apparatus is explained which uses the method of determining regression function of a calibration curve according to the present invention. FIG. 6 is a block diagram showing a general construction of the analyzing apparatus of the invention. Reference numeral 10 designates a measurement means, which measures and detects a signal (some physical quantity such as optical density and electric signal) corresponding to the quantity of analyte (concentration, or activity). The signal to be detected is produced by an enzymatic or chemical reaction of a liquid sample containing an analyte. As described herein after in EXAMPLE, for example, reflected optical density of dry analytical elements after a sample is spotted thereon is measured as a signal. Input means 12 receives the resulting signal (measured data) and transferred this signal to the output means 14. The output means 14 refers a calibration curve stored in a memory (RAM) 22 to calculate an analytical value (concentration) and output it.

Reference numeral 16 denotes a processor which processes operations for determining a regression function of a calibration curve. Reference numeral 18 stands for ROM (which may be a recording medium such as a floppy disc, a hard disc, and an optical magnetic disc) storing algorithm of the method of preparing a calibration curve according to the present invention. The ROM 18 also stores an operation program of the analyzing apparatus. The processor 16 receives analytical measured values (signals) from the input means 12, together with corresponding known concentration or content of the analyte contained in the standard samples, and operates the regression function of calibration curve based on the program stored in ROM 18. While analytes concentrations of standard samples given as known concentrations are input by input means 12, they may be by other input means such as a keyboard and a magnetic reader. Reference numeral 20 stands for a calibration curve generator which generates a calibration curve based on the regression curve determined by the processor 16. The calibration curve thus prepared is input to and stored in the memory (RAM) 22, which may be a recording medium such as a floppy disc, hard disc and optical magnetic disc.

When the analytical measured values such as O.D. of a test sample to be analyzed are input by the input means 12, after the calibration curve is prepared, the output means 14 calculates and outputs the concentration of analyte corresponding the measured values (signals) in the test sample with referring the calibration curve stored in RAM 22.

Figure 7:
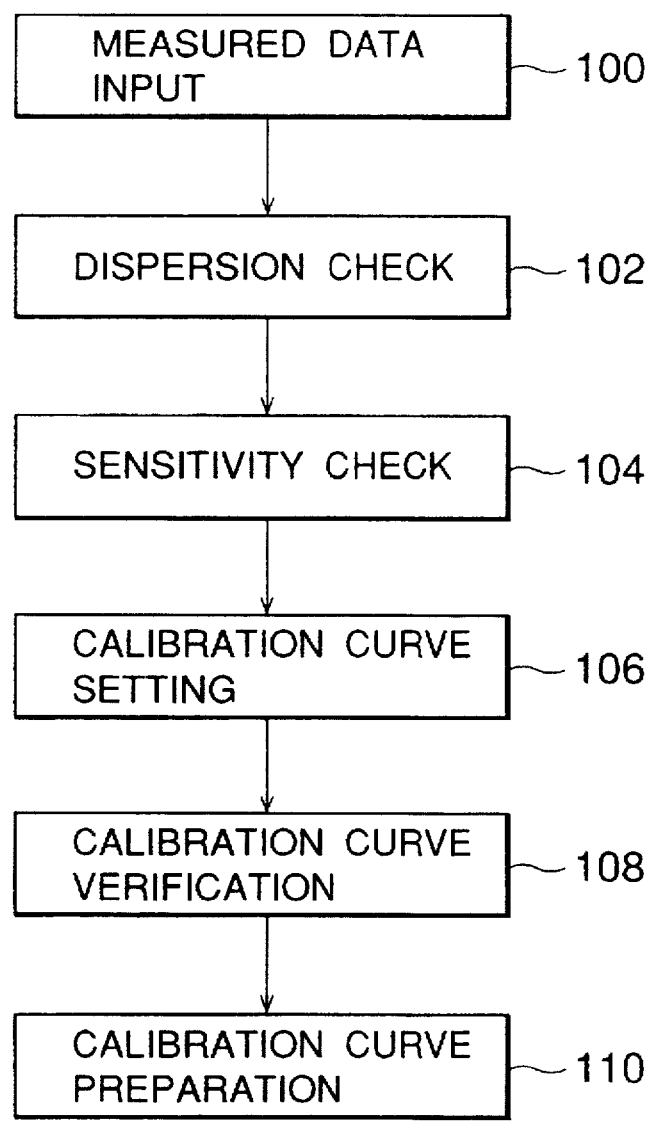
FIG. 7 is a flow chart explaining actions in the embodiment of the analyzing apparatus according to the present invention.

FIG. 7 is a flow chart for preparing a calibration curve in this analyzing apparatus. At first, various concentrations of standard samples (levels 0, 1, 2 and 3) are spotted respectively on to plural dry analytical elements. Measurement means 10 measures the reflected optical densities of the elements. When the analytical measured values (dODr)s are input (step 100), dispersions of the analytical measured values of respective levels are checked (step 102). In this checking, if the standard deviations (S.D.) of the measured data of respective levels of the standard samples exceed predetermined thresholds, the dispersion(s) is interpreted as unacceptable and the subsequent operations are stopped. For examples, if a standard sample solution is not spotted on a dry analytical element in error, or if a standard sample solution is not uniform, there shows wide standard deviation (S.D.) exceeding predetermined threshold. In such a case, the subsequent operations are stopped. In the case where the standard deviations become within the predetermined thresholds by deleting the minimum or maximum values of the measured value (data), the subsequent operations may be allowed to proceed by deleting such data and assuming the remaining data effective for the respective level.

After the dispersions of the analytical measured values of respective levels are judged not to exceed the threshold values, sensitivity check is carried out (step 104). Here, ranking of the averages of the analytical measured values (dODr)s at respective levels are checked whether the ranking is in the order as anticipated. For example, when the anticipated ranking is:

[measured value $q_0$, at level 0]

>[measured value $q_1$, at level 1]
>[measured value $q_2$, at level 2]
>[measured value $q_3$, at level 3], the ranking is checked whether as anticipated. If the ranking is not as expected, preparation of the calibration curve is stopped because the standard samples may be wrong.

When Step 104 is cleared, calibration curves for respective levels are to be determined (Step 106), according to the method of determining calibration curves of the present invention, by use of nominal values $p_i$ for known concentrations and measured values $q_i$ (dODr) at respective levels. In Step 106, the following formulae are to be established for X (concentration) and Y (dODr).

at $q_0 \geq Y \geq q_1$, $X=e\cdot Y^2+f\cdot Y+g$ at $q_1 \geq Y \geq q_2$, $X=(\ln Y-d)/b$ at $q_2 \geq Y \geq q_3$, $X=l\cdot Y^2+m\cdot Y+n$ The following respective coefficients are to be calculated.

$b=(\ln q_2-\ln q_1)/(p_2-p_1)=|\ln(q_2/q_1)|/(p_2-p_1)$ $d = \ln q_2 - b \cdot p_2 = (p_2 \cdot \ln q_1 - p_1 \cdot \ln q_2)/(p_2 - p_1)$ $e = |1/(b \cdot q_1) - (p_1 - p_0)/(q_1 - q_0)|/(q_1 - q_0)$ $f = 1/(b \cdot q_1) - 2e \cdot q_1$ $g = p_0 - e \cdot q_0^2 - f \cdot q_0$ $l = |1/(b \cdot q_2) - (p_3 - p_2)/(q_3 - q_2)|/(q_2 - q_3)$ $m = 1/(b \cdot q_2) - 2 \cdot l \cdot q_2$ $n = p_2 - l \cdot q_2^2 - m \cdot q_2$ From the calculated coefficients, verifications for the low concentration region ($q_0 \geq Y \geq q_1$) and high concentration region ($q_2 \geq Y \geq q_3$) are made (Step 108). When $q_0 > -f/(2 \cdot e) > q_1$, the regression function $X = e \cdot Y^2 + f \cdot Y + g$ for the low concentration region has an extreme value (local maximum value) between $q_0$ and $q_1$. In this case, the regression function cannot be applicable for the calibration curve since two concentrations (X)s may appear for one analytical measured value (Y).

Similarly, when $q_2 > -m/(2 \cdot l) > q_3$, the regression function $X = l \cdot Y^2 + m \cdot Y + n$ at the high concentration region has an extreme value (local minimum value) between $q_2$ and $q_3$. In this case, the regression function cannot be applicable for the calibration curve. Only when the above two cases are not found in the established formulae, the calibration curve is verified.

After the verification of Step 108 is cleared, the regression functions obtained are sent to the calibration curve generator 20 in which the calibration curve is prepared (Step 110). The prepared calibration curve is stored in RAM 22. When analytical measured values of a test sample are input, the output means finds the analyte concentration in the test sample by referring the calibration curve stored in RAM 22 and outputs the estimated concentration.

A preferable sample analyzing apparatus incorporates a display or alarm device (not shown in FIG. 6) for abnormality (error) when actions for preparing the calibration curve in the above steps are stopped or suspended. Any known display or alarm devices may be used.

EXAMPLES

By use of dry analytical elements for analyzing CRP, which is described in EXAMPLE 2 in Unexamined Japanese Patent Publication (KOKAI) No. 128655/1992, a regression function of a calibration curve was determined and prepared according to the present invention. The analytical elements comprise a reagent layer, an adhesive layer, a spreading layer of woven fabric, which are laminated on a transparent support in this order. In the spreading layer, bound of amylase-anti-CRP IgG and substrate carboxymethyl starch for labeled enzyme amylase are impregnated. In the reagent layer, an indicator composition is contained which detects decomposed products of the substrate carboxymethyl starch. Specifically, the analytical elements were prepared as follows.

(1) Synthesis of Enzyme-Labelled Antibody
(1-1) Preparation of CHM Amylase 5 mg of *Bacillus subtilis* α-amylase was dissolved in 1 ml of a 0.1M glycerophosphate (pH 6.3), and 100 µl of a 2 mg/ml solution of |4-(maleimidomethyl)cyclohexane-1-carboxylic acid| succinimide ester (CHMS) in DMF was added thereto and allowed to react at room temperature for one hour. The reaction mixture was introduced into a Sephadex G-25 column and a 0.1M glycerophosphate (pH 6.3) solution was passed through the column to provide an eluted fraction containing 4-(maleimidomethyl)cyclohexane-1-carboxyamido α-amylase (CHM amylase).

(1-2) Preparation of Anti-CRP Mouse IgG F(ab')$_2$

300 µg of Papain was added to 10 mg of anti-CRP mouse IgG (in 2 ml of 0.1M acetate buffer (pH 5.5)), and stirred at 37° C. for 18 hours. A 0.1N NaOH solution was added to the reaction liquid to adjust the pH value thereof to pH 6.0. The liquid was then introduced into a AcA-44 gel column preliminarily equilibrated with a 0.1M phosphate buffer (pH 6.3) containing 1 mM EDTA, followed by elution with the aforementioned phosphate buffer solution. The peak portion of the eluate having molecular weights of approximately 100,000 was collected and concentrated to 1 ml to obtain the objective anti-CRP mouse IgG F(ab')$_2$.

(1-3) Preparation of Bound of α-amylase-Anti-CRP Mouse IgG Fab'

100 µl of a 10 mg/ml aqueous solution of 2-mercaptoethylamine HCl salt was added to 1 ml of a 0.1M phosphate buffer (containing 1 mM EDTA, pH 6.0) containing 6 mg of the anti-CRP mouse IgG F(ab')2 prepared in step (1-2) and stirred at 37° C. for 90 minutes. The reaction mixture was subjected to gel filtration by a Sephadex G-25 column which was preliminarily equilibrated with a 0.1M phosphate buffer (pH 6.3) to remove unreacted 2-mercaptoethylamine to obtain HS-Fab'. 2 mg of the CHM α-amylase prepared by the step (1-1) were added to HS-Fab' to react at 37° C. for 90 minutes. The reaction mixture was then subjected to gel filtration using the AcA-34 column equilibrated with a 0.1M phosphate buffered 5 mM calcium chloride solution (pH 7.0) to collect a fraction having molecular weights of not less than 200,000, and the fraction was concentrated to obtain the objective conjugate of α-amylase and anti-CRP mouse IgG Fab'.

(2) Preparation of Analytical Elements

A reagent solution containing a cross-linking reagent was coated onto a colorless and transparent polyethylene terephthalate (PET) sheet (support) coated with a gelatin undercoating and having a thickness of 180 µm. The sheet was then dried, forming a reagent layer wherein the respective components had the coverages as set forth below.

| | |
|---|---|
| Alkali-treated gelatin | 14.5 g/m$^2$ |
| Nonylphenoxypolyethoxyethanol (Containing 9 to 10 (average) of Oxyethylene Units) | 0.2 g/m$^2$ |
| Glucose oxidase | 5,000 U/m$^2$ |
| Peroxidase | 15,000 U/m$^2$ |
| Glucoamylase | 5,000 U/m$^2$ |
| 2-(4-hydroxy-3,5-dimethoxyphenyl)-4-[4-(dimethylamino)phenyl]-5-phenethyl-imidazole (Leuco Dye) Acetate | 0.38 g/m$^2$ |
| Bis[(vinylsulfonylmethylcarbonyl)-amino]methane | 0.1 g/m$^2$ |

An adhesive layer was coated onto the reagent layer to have the following coverage, and then dried.

| | |
|---|---|
| Alkaline-treated gelatin | 14.5 g/m$^2$ |
| Bis[(vinylsulfonylmethylcarbonyl)amino]-methane | 0.1 g/m$^2$ |

Then, an aqueous solution containing the following reagent was coated over the surface of the adhesive layer to have the following coverage to swell the gelatin layer and a tricot knitted cloth made by knitting PET spun yarn of 36 gage corresponding to 50 deniers and having a thickness of about 250 μm was then laminated thereon, by pressing with a uniform light pressure to form a porous spreading layer.

| | |
|---|---|
| Nonylphenoxypolyethoxyethanol (Containing 9 to 10 (average) of Oxyethylene Units) | 0.15 g/m$^2$ |
| Bis[(vinylsulfonylmethylcarbonyl)amino]-methane | 0.4 g/m$^2$ |

Thereafter, a substrate layer was formed by coating a substrate, followed by drying, to have the following coverages, to prepare the multi-layered analysis element for the quantitative analysis of CRP.

| | |
|---|---|
| Carboxymethyl starch | 4 g/m$^2$ |
| Nonylphenoxypolyethoxyethanol (Containing 9 to 10 (average) of Oxyethylene units) | 0.2 g/m$^2$ |

On the tricot knitted cloth layer, which served both a substrate layer and a spreading layer, a solution of the amylase-anti-CRP IgG conjugate (Synthesis Example (1)) in ethanol was coated and dried to provide a coverage of 3 mg/m$^2$. The analytical element prepared in this way was cut into chips of 15 mm×15 mm each, and each chip was placed in a slide frame described in Unexamined Japanese Patent Publication (KOKAI) No. 63452/1982 to prepare an immunoassay slide for the analysis of CRP.

(3) Measurement

On the immunoassay slide, 10 μl of a sample solution (50 mM glycerophosphate buffer: pH 7) containing a known amount of CRP was spotted and the slide was maintained at 37° C. The optical density of the reflected light having a central wavelength of 650 nm was measured from the PET support side. The differences in optical density ($\Delta OD_{6-4}$, dODr) of the reflected lights measured respectively after the lapse of 4 minutes and 6 minutes from spotting is shown in TABLE 3 together with the logarithmic values.

TABLE 3

| Concentration (mg/dL) | dODr | ln (dODr) |
|---|---|---|
| *0.00 | 0.2460 | −1.444 |
| 0.23 | 0.2313 | −1.464 |
| 0.47 | 0.2289 | −1.475 |
| 0.70 | 0.2195 | −1.516 |
| 0.93 | 0.2140 | −1.542 |
| *1.40 | 0.2003 | −1.608 |
| 1.87 | 0.1824 | −1.702 |
| 2.33 | 0.1591 | −1.838 |
| 2.80 | 0.1522 | −1.882 |
| 3.77 | 0.1187 | −2.131 |
| *4.73 | 0.0993 | −2.310 |
| 5.70 | 0.0853 | −2.462 |
| 6.67 | 0.0732 | −2.615 |
| 7.83 | 0.0657 | −2.723 |
| 9.00 | 0.0625 | −2.772 |
| *10.17 | 0.0587 | −2.836 |
| 11.33 | 0.0590 | −2.831 |

Figure 8:
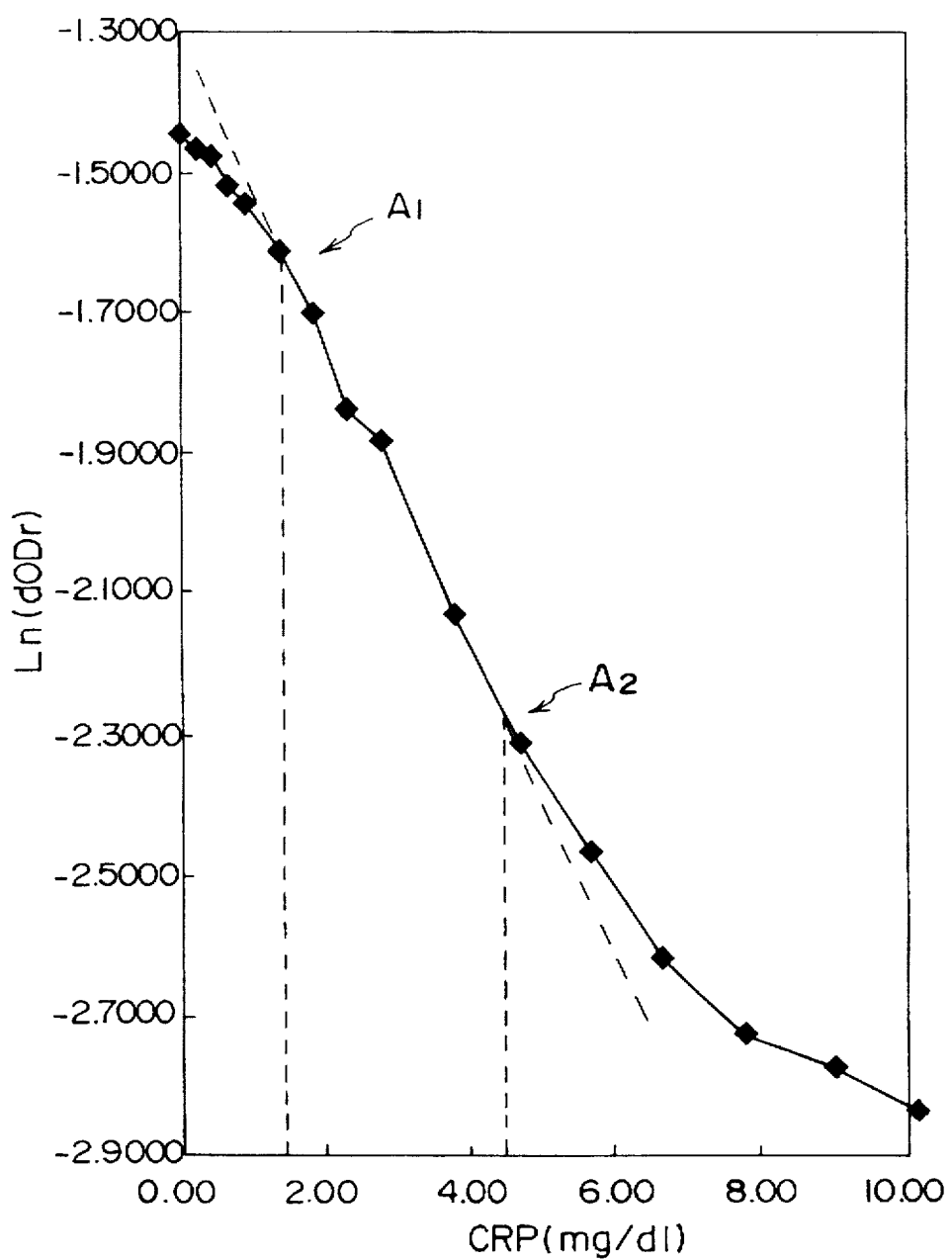
FIG. 8 is a determined calibration curve of EXAMPLE plotting CRP concentration and dODr.

FIG. 8 is a graphical presentation of TABLE 3. The intermediate concentration region constituting a linear part in FIG. 8 is between Point $A_1$(X=1.4 mg/dl) and Point $A_2$ (X=4.7 mg/dl). Here, by use of the concentrations and the analytical measured values (dODr) of the sample solutions of * marks in TABLE 3, $A_0$, $A_1$, $A_2$ and $A_3$ are represented. That is:

$A_0$: $p_0$=0.00, $q_0$=0.2360
$A_1$: $p_1$=1.4, $q_1$=0.2003
$A_2$: $p_2$=4.7, $q_2$=0.0993
$A_3$: $p_3$=10.2, $q_3$=0.0587

Then, the following formulae are established.

at $q_0 \geq Y \geq q_1$, $X = e \cdot Y^2 + f \cdot Y + g$ at $q_1 \geq Y \geq q_2$, $X = (\ln Y - d)/b$ at $q_2 \geq Y \geq q_3$, $X = l \cdot Y^2 + m \cdot Y + n$ The respective coefficients are calculated. From Equations (4), (5), (12), (13), (14), (20), (21) and (22) described previously, the values of the coefficients are as follows.

Figure 9:
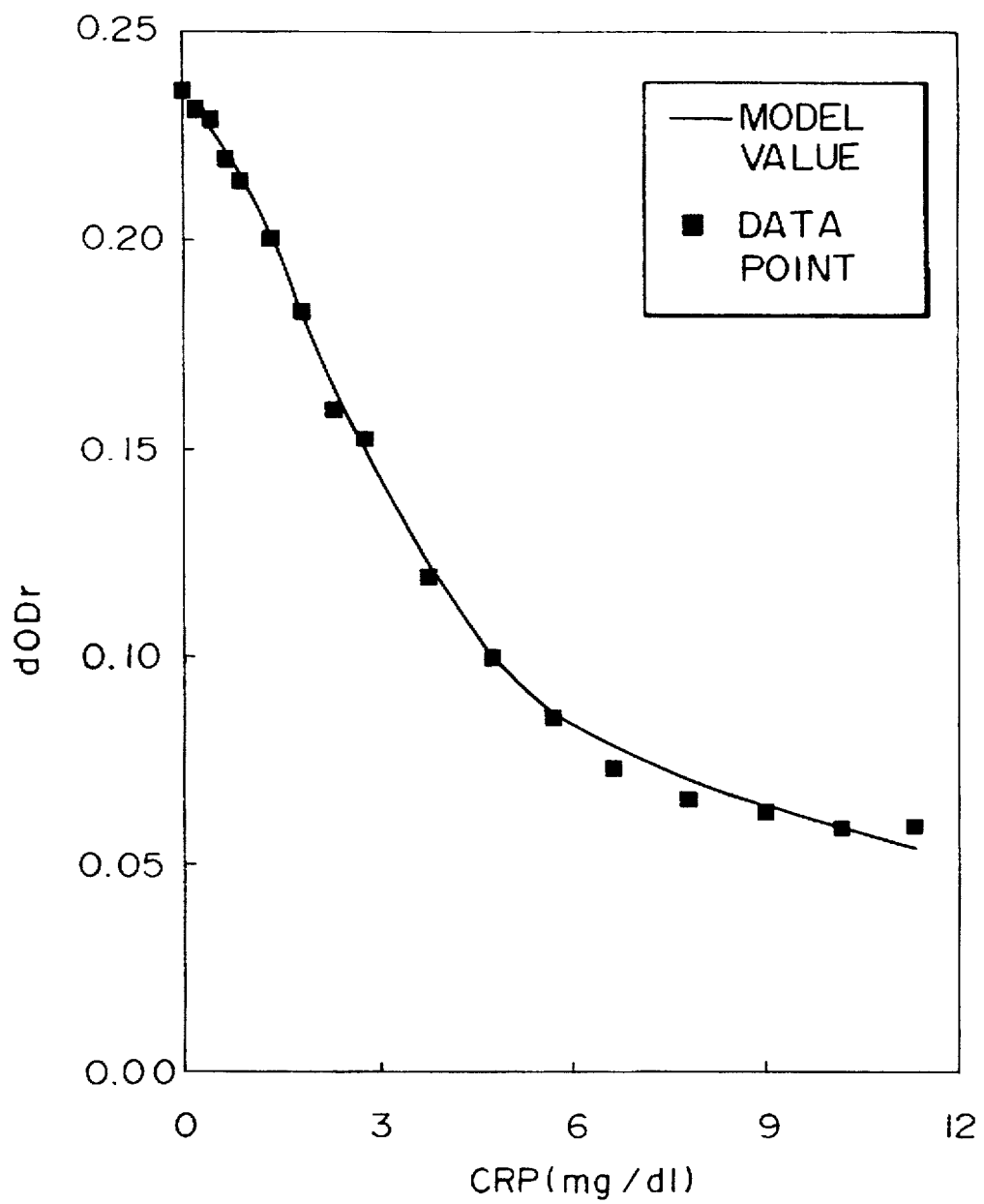
FIG. 9 is a regression curve for analyzing CRP prepared in EXAMPLE by a method of preparing a regression function of a calibration curve according to the present invention.

$b = (\ln q_2 - \ln q_1)/(p_2 - p_1) = -0.210532$ $d = \ln q_2 - b \cdot p_2 = -1.313295$ $e = [1/(b \cdot q_1) - (p_1 - p_0)/(q_1 - q_0)]/(q_1 - q_0)$ $f = 1/(b \cdot q_1) - 2e \cdot q_1 = 149.84713$ $g = p_0 - e \cdot q_0^2 - f \cdot q_0 = -11.23075$ $l = [1/(b \cdot q_2) - p_3 - p_2)/(q_3 - q_2)]/(q_2 - q_3) = 2115.1352$ $m = 1/(b \cdot q_2) - 2 \cdot l \cdot q_2 = -467.8245$ $n = p_2 - l \cdot q_2^2 - m \cdot q^2 = 30.331081$ FIG. 9 is the calibration curve depicted with these coefficients. The model formula values agree with the measured data points shown by ■ quite well for the whole concentration region.

Figure 10:
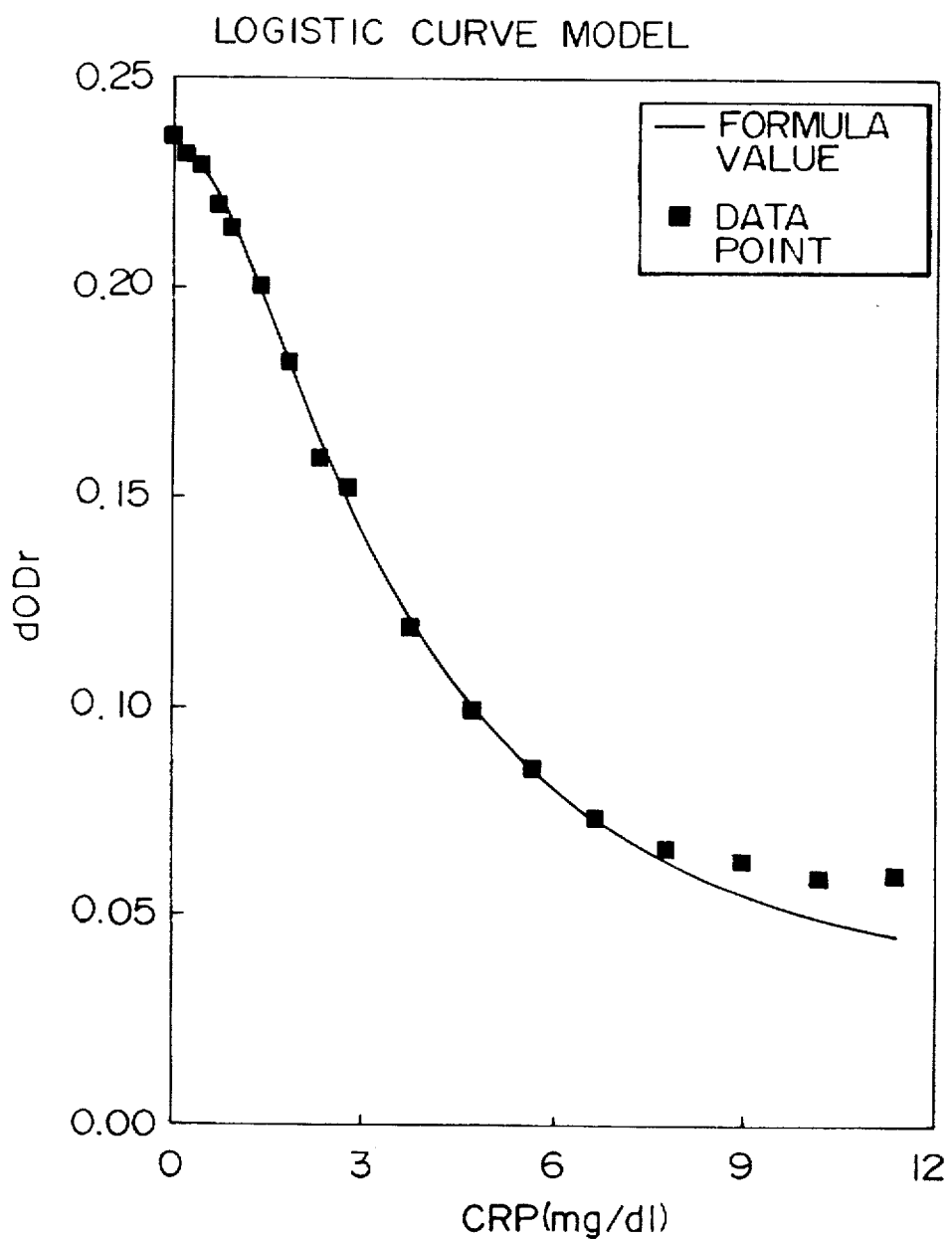
FIG. 10 is a regression curve, as a comparative Example, prepared by a conventional logistic curve model using the data of TABLE 3.

As a COMPARATIVE EXAMPLE, a calibration curve for the data of TABLE 3 was prepared by use of a conventional logistic curve model. FIG. 10 is the resulting calibration curve. As seen, the model formula values differ substantially from the measured data points in the high concentration region. In contrast, the calibration curve of FIG. 9 according to the present invention agrees quite well with the measured experimental data points even in the high concentration region.

As will be appreciated from the foregoing, one sigmoid calibration curve is split into three parts of low concentration region represented by a high order function, intermediate concentration region represented by an exponential function and high concentration region represented by a high order function, according to the present invention. The boundary condition of the adjacent two functions is so set that the two functions have an equal slope at the boundary point, thereby, regression functions of the calibration curves in respective regions are found. Accordingly, the number of standard samples which are to be analyzed for finding a calibration curve can be small while the calibration curve found is of high accuracy.

What is claimed is:

1. A method for determining a regression function of a calibration curve for quantitative analysis of an analyte comprising:

providing standard samples containing known concentrations of analyte, measuring the analytical values of the standard samples, plotting, for each of the standard samples, the value of the known concentration versus the logarithm of the value of the measured analytical value as a point on the calibration curve, determining an intermediate concentration range over which there is a linear relationship between the known concentrations of the standard samples and the logarithmic values of the corresponding measured analytical values, determining a low concentration range extending from the lower concentration end of the intermediate concentration range to a minimum concentration of analyte, determining a high concentration range extending from the higher concentration end of the intermediate concentration range to a maximum concentration of analyte, representing the calibration curve for the intermediate concentration range by an exponential function, representing the calibration curve for the low concentration range by a multi-degree function, representing the calibration curve for the high concentration range by a multi-degree function, and setting boundary conditions that at the boundary points between the multi-degree functions and the exponential function, the values of the first derivative of the multi-degree function and the first derivative of the exponential function are identical, whereby the functions of the calibration curve for the intermediate, low and high concentration regions are determined.

2. The method of claim 1, wherein the multi-degree functions representing said low concentration region and said high concentration region are quadratic functions.

3. A method of preparing a regression function of a calibration curve for quantitative analysis of an analyte, comprising the steps of:

(a) providing standard samples containing known concentrations of analyte, measuring the analytical values of the standard samples and plotting respective concentrations ($p_i$) of the analyte in the standard sample and the logarithmic values ($\log q_i$) of the corresponding analytical measured values ($q_i$) on the rectangular coordinate system;

(b) finding an intermediate concentration region ($p_{1-p2}$) which constitutes a linear portion in this semi-logarithmic graph;

(c) expressing the part of calibration curve of this intermediate concentration region ($p_{1-p2}$) as $$Y=exp(b \cdot X+d)$$

which means $$X=(ln\ Y-d)/b \quad (1)$$

wherein

Y is the analytical measured value ($q_i$) such as optical density or other physical quantity, X is the concentration of the analyte in the standard sample ($p_i$), and b and d are coefficients;

(d) expressing the part of calibration curve of the low concentration region (from the minimum concentration $p_0$ in the standard samples to the concentration $p_1$) as $$X=e \cdot Y^2+f \cdot Y+g \quad (2)$$

wherein e, f and g are coefficients;

(e) expressing the part of calibration curve of the high concentration region (from the concentration $p_2$ to the maximum concentration $p_3$ in the standard samples) as $$X=l \cdot Y^2+m \cdot Y+n \quad (3)$$

wherein l, m and n are coefficients;

(f) setting boundary conditions where the differentiated value (dX/dY) of Equation (1) at the coordinate ($p_1$, $q_1$) is equal to the differentiated value (dX/dY) of Equation (2) at the coordinate ($p_1$, $q_1$) and where the differentiated value (dX/dY) of Equation (2) at the coordinate ($p_2$, $q_2$) is equal to the differentiated value (dX/dY) of Equation (3) at the coordinate ($p_2$, $q_2$); and (g) calculating respective coefficients in Equations (1), (2) and (3) and finding therefrom the continuous regression function of the calibration curve for the whole concentration region covering from $p_0$ to $p_3$.

4. A method of preparing a regression function of a calibration curve for quantitative analysis of an analyte, comprising the steps of:

(a) providing standard samples containing known concentrations of analyte, measuring the analytical values of the standard samples and; providing an intermediate concentration region ($p_1-p_2$) which is defined as the region of linear portion in a semi-logarithmic graph in which respective concentrations ($p_i$) of the analyte in the standard samples and the logarithmic values ($\log q_i$) of the corresponding analytical measured values ($q_i$) on a rectangular coordinate system, said linear portion having the most proximate concentrations $p_1$ and $p_2$ at both ends;

(b) expressing the part of calibration curve of an intermediate concentration region ($p_1-p_2$) as $$Y=exp(b \cdot X+d)$$

which means $$X=(ln\ Y-d)/b \quad (1)$$

wherein

Y is the analytical measured value ($q_i$) such as optical density or other physical measuring quantity, X is the concentration of the analyte in the standard sample ($p_i$), and b and d are coefficients;

(c) expressing the part of calibration curve of the low concentration region (from the minimum concentration $p_0$ in the standard sample to the concentration $p_1$) as $$X=e \cdot Y^2+f \cdot Y+g \quad (2)$$

wherein e, f and g are coefficients;

(d) expressing the part of calibration curve of the high concentration region (from the concentration $p_2$ to the maximum concentration $p_3$ in the standard sample) as $$X=l \cdot Y^2+m \cdot Y+n \quad (3)$$

wherein l, m and n are coefficients;

(e) setting boundary conditions where the differentiated value (dX/dY) of Equation (1) at the coordinate/($p_1$, $q_1$) is equal to the differentiated value (dX/dY) of Equation (2) at the coordinate ($p_1$, $q_1$) and where the differentiated value (dX/dY) of Equation (2) at the coordinate ($p_2$, $q_2$) is equal to the differentiated value (dX/dY) of Equation (3) at the coordinate ($p_2$, $q_2$); and (f) calculating respective coefficients in Equations (1), (2) and (3) and finding therefrom the continuous regression function of the calibration curve for the whole concentration region covering from $p_0$ to $p_3$.

5. A method for quantitative analysis of an analyte in a sample comprising, measuring an analytical value of the sample and determining the concentration of the analyte in the sample by comparing the analytical value to a calibration curve;

wherein the calibration curve comprises a continuous regression function of at least three parts:
(a) an intermediate concentration region which is represented by an exponential function and corresponds to a linear portion of a rectangular coordinate system plot of the respective known concentrations ($p_i$) of the analyte in standard samples and the logarithmic values ($\log q_i$) of the corresponding measured analytical values ($q_i$) of the standard samples,
(b) a low concentration region which is represented by a multi-degree function and extends from the lower concentration end of the intermediate concentration region toward a minimum analyte concentration, and
(c) a high concentration region which is represented by a multi-degree function and extends from the higher concentration end of the intermediate concentration region toward a maximum analyte concentration;

wherein adjacent parts of the calibration curve have identical slopes at the boundary between them.

6. A method for quantitative analysis of an analyte in a sample comprising, measuring an analytical value of the sample and determining the concentration of the analyte in the sample by comparing the analytical value to a calibration curve; wherein the calibration curve comprises a continuous regression function determined by the process of claim 1.

7. A method for quantitative analysis of an analyte in a sample comprising, measuring an analytical value of the sample and determining the concentration of the analyte in the sample by comparing the analytical value to a calibration curve; wherein the calibration curve comprises a continuous regression function determined by the process of claim 2.

8. A method for quantitative analysis of an analyte in a sample comprising, measuring an analytical value of the sample and determining the concentration of the analyte in the sample by comparing the analytical value to a calibration curve; wherein the calibration curve comprises a continuous regression function determined by the process of claim 3.

9. A method for quantitative analysis of an analyte in a sample comprising, measuring an analytical value of the sample and determining the concentration of the analyte in the sample by comparing the analytical value to a calibration curve; wherein the calibration curve comprises a continuous regression function determined by the process of claim 4.

* * * * *